(12) United States Patent
Payne et al.

(10) Patent No.: US 8,181,938 B2
(45) Date of Patent: May 22, 2012

(54) HUMIDIFICATION CHAMBERS

(75) Inventors: Simon Robert Payne, Godalming (GB); Keethan Fernando, Bracknell (GB)

(73) Assignee: Intersurgical AG, Vaduz (LI)

( * ) Notice: Subject to any disclaimer, the term of this patent is extended or adjusted under 35 U.S.C. 154(b) by 625 days.

(21) Appl. No.: 12/376,818

(22) PCT Filed: Aug. 10, 2007

(86) PCT No.: PCT/GB2007/050487
§ 371 (c)(1), (2), (4) Date: Feb. 9, 2009

(87) PCT Pub. No.: WO2008/017893
PCT Pub. Date: Feb. 14, 2008

(65) Prior Publication Data
US 2010/0171229 A1    Jul. 8, 2010

(30) Foreign Application Priority Data
Aug. 10, 2006    (GB) .................................. 0615872.9

(51) Int. Cl.
*B01F 3/04* (2006.01)

(52) U.S. Cl. ...................... 261/5; 261/6; 261/58; 261/70

(58) Field of Classification Search .................. 261/4, 5, 261/6, 49, 58, 70, 119.1, DIG. 65
See application file for complete search history.

(56) References Cited

U.S. PATENT DOCUMENTS

| | | | |
|---|---|---|---|
| 4,051,205 A | 9/1977 | Grant | |
| 4,225,542 A * | 9/1980 | Wall et al. | 261/142 |
| 4,261,353 A * | 4/1981 | Bartels | 128/200.11 |
| 4,529,867 A | 7/1985 | Velnosky | |
| 4,724,104 A * | 2/1988 | Kim | 261/4 |
| 4,913,140 A | 4/1990 | Orec et al. | |
| 4,943,704 A | 7/1990 | Rabenau | |
| 5,195,515 A | 3/1993 | Levine | |
| 5,426,271 A | 6/1995 | Clark et al. | |
| 5,445,143 A | 8/1995 | Sims | |

(Continued)

FOREIGN PATENT DOCUMENTS

AU    468170    1/1976

(Continued)

OTHER PUBLICATIONS

Search Report of corresponding PCT/GB2007/050487, Apr. 2008.

(Continued)

*Primary Examiner* — Charles Bushey
(74) *Attorney, Agent, or Firm* — LeClairRyan, a Professional Corporation

(57) ABSTRACT

A humidification chamber (10) for use in a breathing circuit to humidify gases before inhalation is disclosed. The humidification chamber (10) is adapted to contain a volume of liquid (20), and comprises a gas inlet port (16), a gas outlet port (16) and a fluid inlet (30) for introducing liquid into the humidification chamber (10). The fluid inlet (30) is provided with a filter member (60) including a plurality of exit apertures for enabling flow of liquid through the filter member (60). The filter member (60) also defines a collection chamber (69) that is disposed below the exit apertures, in use, such that foreign objects in the liquid that are unable to pass through the exit apertures fall under the influence of gravity into the collection chamber (69).

24 Claims, 5 Drawing Sheets

U.S. PATENT DOCUMENTS

| | | | |
|---|---|---|---|
| 5,520,854 A * | 5/1996 | Porco et al. | 261/5 |
| 5,598,837 A | 2/1997 | Sirianne | |
| 5,782,258 A | 7/1998 | Herbon | |
| 6,031,968 A | 2/2000 | Holtman | |
| 6,053,482 A * | 4/2000 | Glenn et al. | 261/4 |
| 6,981,514 B2 | 1/2006 | Nishi | |
| 7,047,999 B2 | 5/2006 | Payne | |
| 7,066,452 B2 * | 6/2006 | Rotering et al. | 261/142 |
| 7,694,942 B1 * | 4/2010 | Genera et al. | 261/3 |
| 2002/0030005 A1 | 3/2002 | Crompton | |

FOREIGN PATENT DOCUMENTS

| | | |
|---|---|---|
| DE | 298620 A5 | 3/1992 |
| DE | 29617077 U1 | 1/1997 |
| EP | 0376584 A2 | 7/1990 |
| EP | 0589429 A1 | 3/1994 |
| EP | 2119466 A1 | 11/2009 |
| FR | 2602996 A1 | 2/1988 |
| GB | 2006023 | 5/1979 |
| GB | 1589102 | 5/1981 |
| GB | 2209479 A | 5/1989 |
| GB | 1480786 A | 7/1997 |
| JP | 2001349255 | 3/2000 |
| JP | 3433397 B2 | 8/2003 |
| WO | 0021602 A1 | 4/2000 |
| WO | 02058770 A1 | 8/2002 |
| WO | 2005011785 A1 | 2/2005 |
| WO | 2005079898 A3 | 9/2005 |
| WO | 2008027670 A1 | 3/2008 |

OTHER PUBLICATIONS

Search Report of corresponding GB0715528.6, Nov. 2007.

* cited by examiner

HUMIDIFICATION CHAMBERS

This application is a national stage application under 35 U.S.C. §371 from PCT Application No. PCT/GB2007/050487, filed Aug. 10, 2007, which claims the priority benefit of Great Britain Application No. 0615872.9, filed Aug. 10, 2006.

This invention relates to humidification chambers, and in particular to humidification chambers for use in a breathing circuit to humidify gases before inhalation.

The inhalation by patients of gases lacking sufficient moisture may damage or irritate the respiratory tract, and/or desiccate essential secretions, especially in the case of patients whose upper airways have been bypassed. Gases within a breathing circuit are therefore usually humidified before inhalation using a suitable humidification chamber.

Conventional humidification chambers generally contain a volume of water, and have two ports through which gases enter and exit the humidification chamber, and means for heating the water. Furthermore, many humidification chambers include means for replacing water that is lost from the humidification chamber so as to maintain the level of the water relatively constant. Such means typically takes the form of a fluid inlet including a valve for controlling the flow of liquid into the chamber. The valve typically has a float actuator, whereby the rise and fall of the float actuator, in use, acts to open and close the valve so as to maintain the level of the water in the humidification chamber relatively constant.

A problem associated with conventional humidification chambers, however, is that small foreign objects may be present in the liquid being supplied to the fluid inlet, which then enter the humidification chamber. These small foreign objects may become entrained with the respiratory gases flowing through the humidification chamber, thereby potentially harming the patient. In addition, the small foreign objects may interfere with the functioning of the fluid inlet valve, for instance by restricting movement of the float actuator and/or preventing the formation of an effective seal between a valve seat and an actuating member of the valve.

There has now been devised an improved humidification chamber which overcomes or substantially mitigates the above-mentioned and/or other disadvantages associated with the prior art.

According to a first aspect of the invention, there is provided a humidification chamber for use in a breathing circuit to humidify gases before inhalation, the humidification chamber being adapted to contain a volume of liquid, and comprising a gas inlet port, a gas outlet port and a fluid inlet for introducing liquid into the humidification chamber, wherein the fluid inlet is provided with a filter member including a plurality of exit apertures for enabling flow of liquid through the filter member, and the filter member defines a collection chamber that is disposed below the exit apertures, in use, such that foreign objects in the liquid that are unable to pass through the exit apertures fall under the influence of gravity into the collection chamber.

The humidification chamber according to the invention is advantageous principally because foreign objects within the liquid flowing through the fluid inlet that are too large to pass through the exit apertures will fall under the influence of gravity into the collection chamber, and hence foreign objects that collect within the collection chamber will not impede subsequent flow of liquid through the exit apertures. The present invention therefore reduces the risk of the fluid inlet becoming blocked, as well as reducing the risk of foreign objects becoming entrained with the respiratory gases flowing through the humidification chamber or interfering with the functioning of a fluid inlet valve.

The filter member is preferably formed as a separate component from the fluid inlet, and is preferably fixed relative to the fluid inlet so that the filter member defines a partition within the fluid inlet through which liquid flowing through the fluid inlet necessarily flows.

The filter member may be formed of any material that is suitable for medical applications, but the filter member is preferably formed of injection moulded plastics material. In presently preferred embodiments, the filter member is formed of a relatively rigid plastics material, such as a polycarbonate plastics material, so that the filter member maintains its integrity and shape during normal use of the humidification chamber.

The exit apertures are preferably sufficiently small in order to prevent the passage of a large proportion of the foreign bodies that might be contained within the liquid being supplied to the fluid inlet. However, the exit apertures are preferably also sufficiently large for manufacture of the filter member to be practicable. Furthermore, the exit apertures are preferably sufficiently large to enable an acceptable rate of flow through the fluid inlet during use. The exit apertures preferably each have a length and/or width that is less than 1 mm, more preferably less than 0.7 mm, and most preferably less than 0.5 mm. In presently preferred embodiments, each exit aperture has a width of approximately 0.26 mm and a length of approximately 0.36 mm. The collection chamber is preferably defined by a continuous wall of the filter member, and hence does not include any exit apertures.

The filter member preferably comprises an inlet portion into which liquid from a source of liquid flows, and an outlet portion in which the exit apertures and the collection chamber are formed. The outlet portion preferably has the form of a liquid conduit having exit apertures within its side wall, and a collection chamber is preferably defined by a closed end of the outlet portion. The outlet portion is preferably disposed generally vertically, and the collection chamber is preferably formed at the lowermost end of the outlet portion. The outlet portion is preferably of tubular structure, and is most preferably generally cylindrical. In this arrangement, the outlet portion of the filter member preferably extends along a central, longitudinal axis of the fluid inlet, and is preferably separated from the interior surface of the fluid inlet at all points.

A wall of the filter member preferably comprises a plurality of elongate openings, and a plurality of generally orthogonal ribs that are formed on a surface of that wall and extend across those openings, so as to define an array of exit apertures. Where the outlet portion is of tubular structure, the exit apertures are preferably formed in a side wall of the outlet portion. In this case, the orthogonal ribs are preferably formed on the interior surface of the outlet portion. Furthermore, the elongate openings preferably extend along circumferences of the outlet portion, and the orthogonal ribs are preferably orientated longitudinally along the outlet portion.

The filter member preferably includes an inlet portion that is fixed to the fluid inlet, and is most preferably fixed to an interior surface of the fluid inlet, so that liquid supplied to the fluid inlet necessarily flows through the filter member. Where the fluid inlet has substantially constant cross-sectional dimensions, the outlet portion of the filter member preferably has reduced cross-sectional dimensions relative to the inlet portion so that the outlet portion is separated from the interior surface of the fluid inlet. In presently preferred embodiments, the inlet and outlet portions of the filter member are both cylindrical, and have substantially co-extensive central axes.

In addition, the outlet portion preferably extends a short distance into the interior of the inlet portion, so that a secondary collection chamber is defined about the entrance to the outlet portion.

The humidification chamber preferably includes a valve for controlling the level of liquid within the humidification chamber. In particular, the fluid inlet preferably includes a primary valve seat, and the valve preferably comprises an actuating member that is movable in response to a change in the level of liquid within the humidification chamber between an open configuration in which the actuating member is disengaged from the primary valve seat such that liquid is able to flow through the fluid inlet into the humidification chamber when the liquid within the humidification chamber is below a predetermined acceptable level, and a closed configuration in which the actuating member is engaged with the primary valve seat such that liquid is prevented from flowing through the fluid inlet into the humidification chamber when the liquid within the humidification chamber is at or above the predetermined acceptable level.

In the event that very small foreign objects pass through the exit openings and enter the humidification chamber, these foreign objects may reduce the effectiveness of the seal formed between the actuating member and the primary valve seat so that the valve fails to prevent flow of liquid through the fluid inlet into the humidification chamber. The fluid inlet preferably therefore includes a secondary valve seat, and the actuating member is preferably deformable in response to an increase in the level of liquid within the humidification chamber above the predetermined acceptable level to a deformed configuration in which the actuating member engages the secondary valve seat such that liquid is prevented from flowing through the fluid inlet into the humidification chamber.

Hence, according to a further aspect of the invention, there is provided a humidification chamber for use in a breathing circuit to humidify gases before inhalation, the humidification chamber being adapted to contain a volume of liquid, and comprising a gas inlet port, a gas outlet port, a fluid inlet including a primary valve seat, and a valve having an actuating member that is movable in response to a change in the level of liquid within the humidification chamber between an open configuration in which the actuating member is disengaged from the primary valve seat such that liquid is able to flow through the fluid inlet into the humidification chamber when the liquid within the humidification chamber is below a predetermined acceptable level, and a closed configuration in which the actuating member is engaged with the primary valve seat such that liquid is prevented from flowing through the fluid inlet into the humidification chamber when the liquid within the humidification chamber is at or above the predetermined acceptable level, wherein the fluid inlet includes a secondary valve seat, and the actuating member is deformable in response to an increase in the level of liquid within the humidification chamber above the predetermined acceptable level to a deformed configuration in which the actuating member engages the secondary valve seat such that liquid is prevented from flowing through the fluid inlet into the humidification chamber.

The humidification chamber according to this aspect of the invention is advantageous principally because, in the event that the effectiveness of the seal formed between the actuating member and the primary valve seat is impaired so that the valve fails to prevent flow of liquid through the fluid inlet into the humidification chamber, the actuating member will be deformed by the rising liquid level within the humidification chamber into engagement with the secondary valve seat so as to prevent the flow of liquid through the fluid inlet.

The actuating member is preferably operably linked to a float so as to be movable in response to movement of the float. The force that causes the actuating member to deform into engagement with the secondary valve seat is preferably generated by the buoyancy of the float, which preferably increases as the level of liquid within the humidification chamber increases.

The primary and secondary valve seats are both preferably continuous, and the primary valve seat is preferably disposed within the space that is bordered by the secondary valve seat. In presently preferred embodiments the primary and secondary valve seats are substantially circular in shape, and are preferably disposed in a generally concentric arrangement. Furthermore, the valve is preferably arranged such that the actuating member engages only the primary valve seat in the closed configuration, and the actuating member engages both the primary valve seat and the secondary valve seat in the deformed configuration. Most preferably, the actuating member includes an operative surface that engages the valve seats, in use. This operative surface is preferably substantially flat in the open configuration. The secondary valve seat is preferably therefore disposed a greater distance from the operative surface of the actuating member, relative to the primary valve seat, in the open configuration.

The actuating member may be defined by part of the float. However, in presently preferred embodiments, the actuating member is a separate component from the float. The actuating member is preferably flexible in form, and is preferably formed of a resilient material, such as a thermoplastic elastomer, in order to form a reliable and effective seal with the valve seats.

In presently preferred embodiments, the actuating member has the form of a valve cushion that is engaged with the float, and at least part of the valve cushion is preferably separated from the exterior surface of the float so as to allow deformation of the valve cushion, in use, towards the exterior surface of the float. For instance, the valve cushion may have the form of a cup that is mounted within a recess in an upper surface of the float. In this case, a base of the valve cushion preferably defines the operative surface, and is preferably separated from the base of the recess in order to allow deformation of the valve cushion during use.

The fluid inlet preferably extends through an opening in a wall of the humidification chamber. The fluid inlet is preferably adapted at one end for connection to a source of liquid, and at the other end for introducing liquid into the humidification chamber. Most preferably, the fluid inlet includes an exit orifice through which liquid may enter the humidification chamber, and the valve seats preferably extend about this exit orifice. The exit orifice is preferably of reduced diameter relative to the remainder of the fluid inlet, and the fluid inlet preferably includes a tapered end portion that leads to the exit orifice. The primary and secondary valve seats are preferably formed integrally with the fluid inlet, and preferably have narrow operative surfaces.

The float is preferably slidably mounted relative to the fluid inlet. Most preferably, the float is slidably mounted relative to a guide sleeve. The guide sleeve preferably extends from an interior surface of the humidification chamber, and the fluid inlet is preferably disposed within the guide sleeve. In presently preferred embodiments, at least part of the float is slidably mounted within guide sleeve, and the guide sleeve preferably includes longitudinal ribs on its interior surface that define channels along which liquid may flow down the exterior surface of the float.

The liquid is normally water, or a suitable aqueous solution. During use, the level of liquid within the humidification chamber will gradually reduce as the gases flowing through the humidification chamber are humidified. Most preferably, the valve is adapted to maintain the level of liquid within the humidification chamber within a relatively narrow range about the predetermined acceptable level.

The humidification chamber preferably comprises an upper portion that is formed of plastic material, most preferably by injection moulding, and a base formed of a good heat conductor, such as a suitable metal, that together define an enclosure for containing the liquid. The base is preferably generally circular in shape, and the upper portion preferably has a generally cylindrical side wall. The gas inlet port and gas outlet port are preferably formed in an upper wall of the humidification chamber, and preferably comprise upstanding tubular connectors that are adapted for connection to conventional respiratory connectors and tubing. The fluid inlet and the guide sleeve are preferably formed integrally with the upper portion of the humidification chamber, and are preferably situated generally centrally in an upper wall of the humidification chamber.

Preferred embodiments of the invention will now be described in greater detail, by way of illustration only, with reference to the accompanying drawings, in which FIG. 1 is a first cross-sectional view of a humidification chamber according to the invention, in which a primary float is acting to maintain a fluid inlet valve in a closed configuration;

Figure 1:
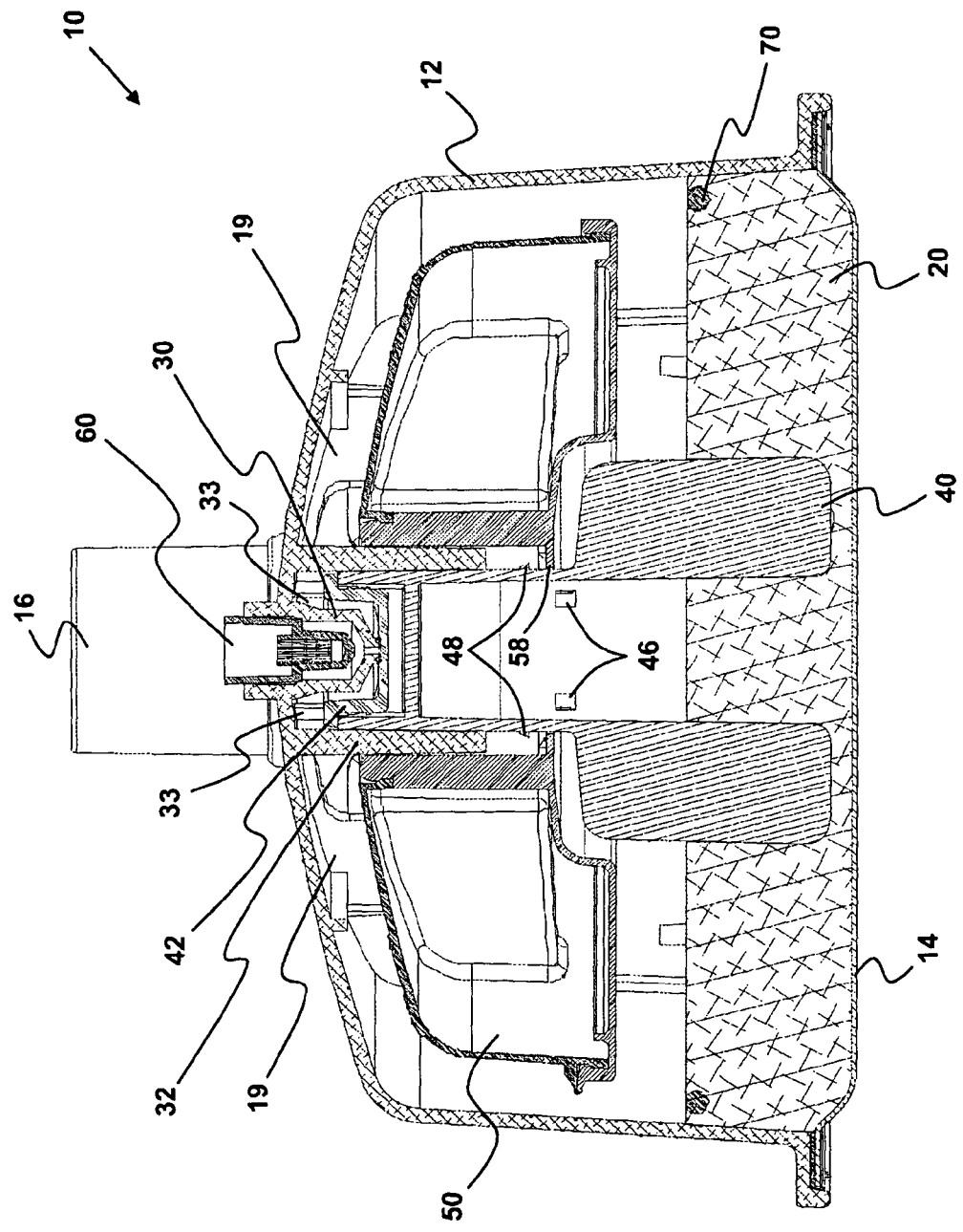
Figure 2:
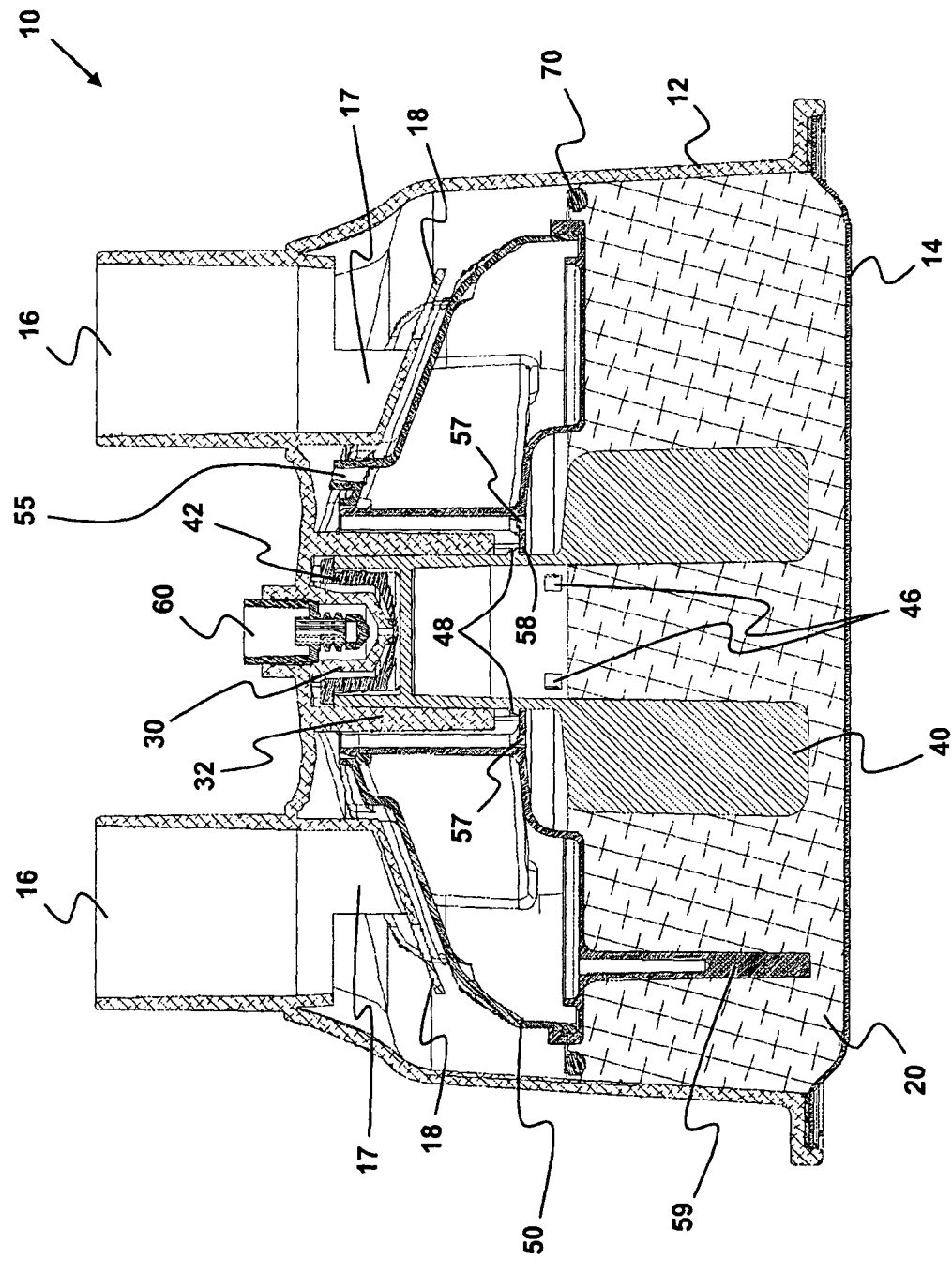
FIG. 2 is a second cross-sectional view of the humidification chamber, in which a secondary float is acting to maintain a fluid inlet valve in a closed configuration.

FIGS. 1 and 2 show a humidification chamber according to the invention, which is generally designated 10. The humidification chamber 10 comprises a body 12 that is injection moulded in a transparent plastics material, and a metal base 14 fixed to an open lower end of the body 12. The body 12 and the base 14 of the humidification chamber 10 cooperate to define an enclosure for containing, in use, a volume of water 20.

The body 12 of the humidification chamber 10 comprises a generally cylindrical, but slightly tapered, side wall that is fixed at its lower end to the periphery of the base 14, and an upper wall that has the general shape of a shallow dome. The base 14 of the humidification chamber 10 has the form of a circular disc, with an upturned rim that is sealed to a flange at the lower end of the side wall of the body 12.

Two inlet/outlet ports 16 that have the form of 22 mm tubular connectors extend upwardly from openings in the upper wall of the humidification chamber 10. Each inlet/outlet port 16 also includes a hemi-cylindrical extension 17 and a circular end baffle 18 within the enclosure of the humidification chamber 10, which together define a lower opening that faces the side wall of the humidification chamber 10. In addition, the humidification chamber 10 includes four baffles 19 (two of which are visible in FIG. 1) that are each formed integrally with the body 12 of the humidification chamber 10, and each extend downwardly from the interior surface of the upper wall. Each baffle 19 is arcuate in its horizontal dimension, and extends horizontally between an interior surface of the side wall of the humidification chamber 10 and a position adjacent to, but separated from, the guide sleeve 32.

Figure 5:
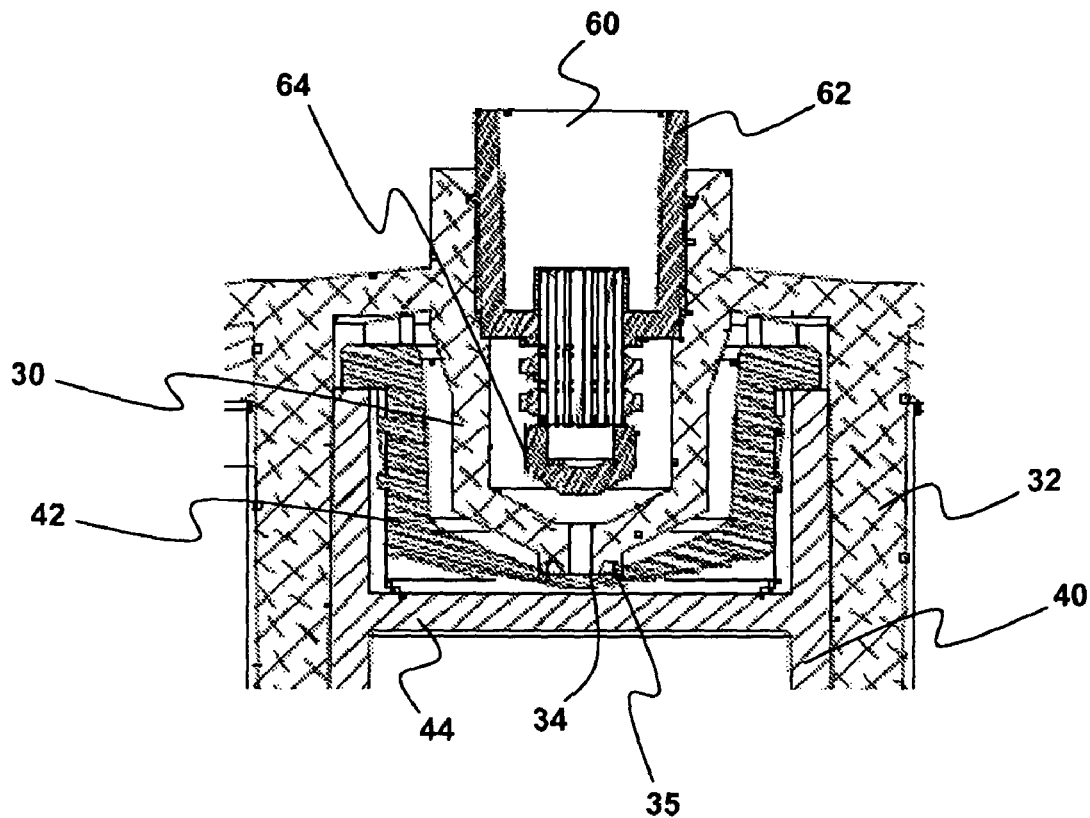
FIG. 5 is a fragmentary cross-sectional view of a fluid inlet valve of the humidification chamber.

Referring now also to FIG. 5, the humidification chamber 10 also comprises a fluid inlet 30 that extends through an opening in the centre of the upper wall of the humidification chamber 10. The fluid inlet 30 comprises an upper cylindrical portion with an open upper end, an intermediate cylindrical portion of reduced diameter, and a tapered lower end portion that terminates within the humidification chamber 10 with a lower opening of significantly reduced diameter relative to the open upper end.

As shown most clearly in FIG. 5, the exterior surface of the fluid inlet 30 that surrounds the lower opening comprises two concentric projections, the inner projection being of greater extent than the outer projection. These concentric projections each terminate with a relatively narrow edge, and these relatively narrow edges define an inner valve seat 34 and an outer valve seat 35, which are both adapted to form a seal with an elastomeric valve cushion 42 that is described in more detail below.

Figure 6:
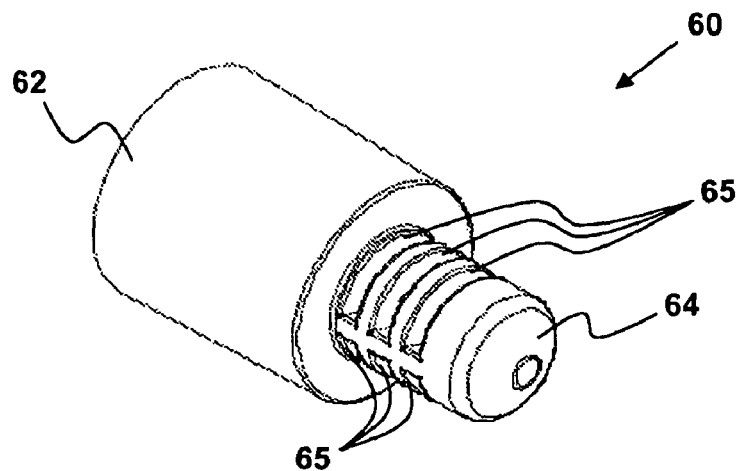
FIG. 6 is a perspective view of a fluid inlet filter of the humidification chamber.
Figure 7:
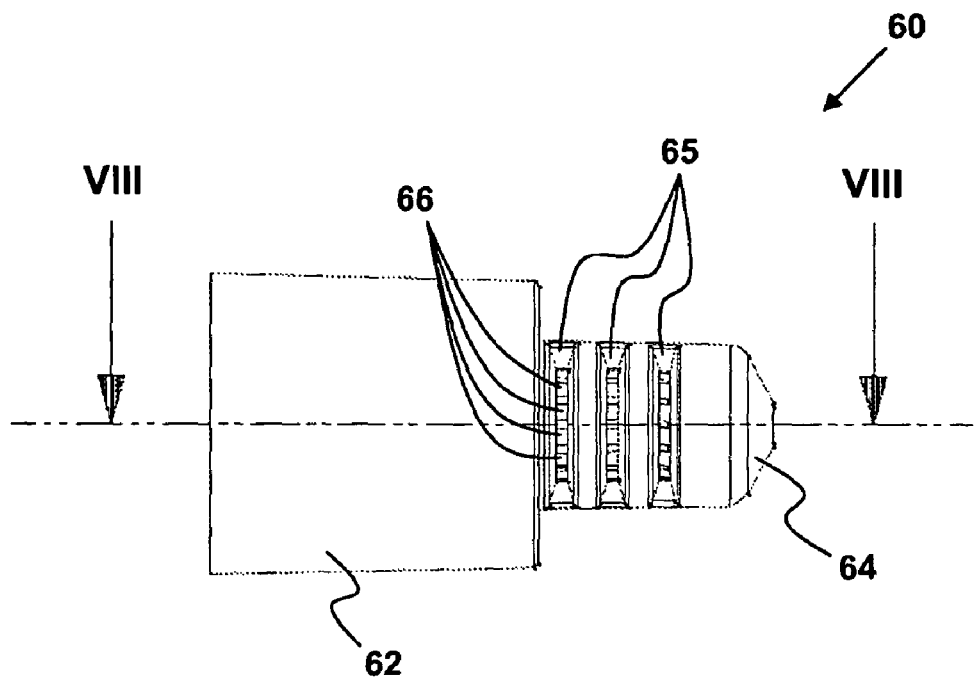
FIG. 7 is a side view of the fluid inlet filter.
Figure 8:
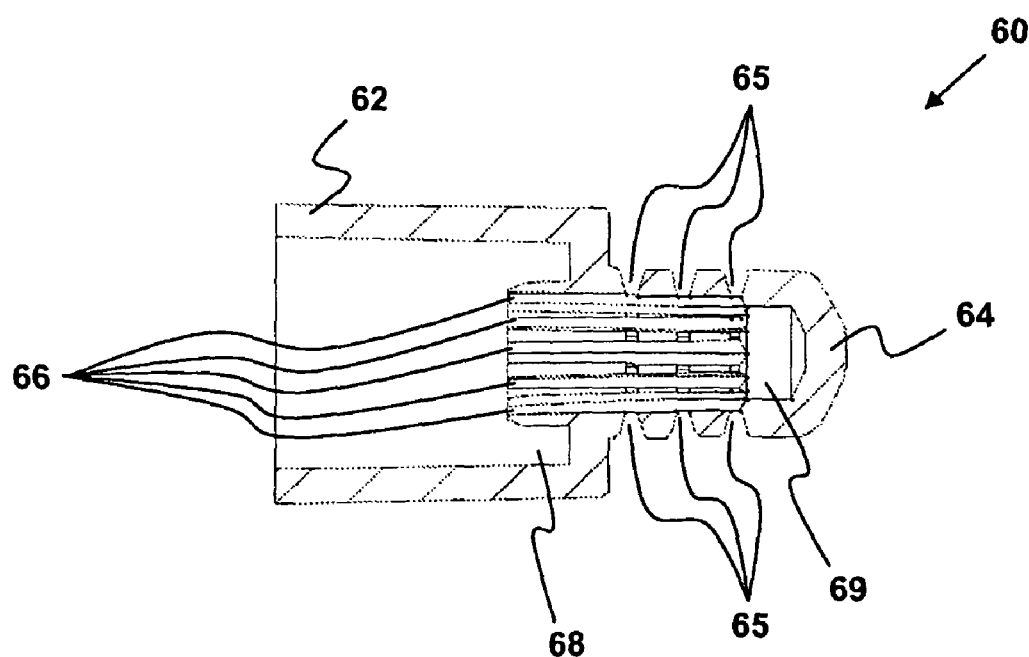
FIG. 8 is a cross-sectional view, along the line VIII-VIII in FIG. 7, of the fluid inlet filter.

A filter 60 is fixed within the fluid inlet 30 so that water flowing through the fluid inlet 30 necessarily flows through the filter 60. The filter 60 is shown most clearly in FIGS. 6, 7 and 8, and comprises a cylindrical inlet portion 62, and a cylindrical outlet portion 64 of reduced diameter. The inlet portion 62 has an open end, and an end from which the outlet portion 64 projects. The outlet portion 64 has an open end situated a short distance within the inlet portion 62, so as to define an annular, first collection chamber 68 of the filter 60, and the outlet portion 64 extends through the end wall of the inlet portion 62. The projecting part of the outlet portion 64 has a closed end and a side wall that includes six elongate openings 65, which each reduce gradually in width before leading into the interior of the outlet portion 64. The openings 65 are arranged in three circumferentially-extending pairs at equally spaced positions along the longitudinal axis of the outlet portion 64. Furthermore, longitudinal members 66 that extend perpendicularly across the openings 65 are formed on the interior surface of the outlet portion 64, so that an array of apertures is defined in the side wall of the outlet portion 64. An end portion of the outlet portion 64 does not include any apertures, and hence defines a second collection chamber 69 of the filter 60. In this embodiment, the filter 60 is injection moulded in polycarbonate plastics material, and each aperture has a width of approximately 0.26 mm and a length of approximately 0.36 mm.

The inlet portion 62 of the filter 60 is received with an interference fit within the upper portion of the fluid inlet 30, and is fixed using suitable adhesive so that there is a seal between the external surface of the inlet portion 62 of the filter 60 and the interior surface of the upper portion of the fluid inlet 30. The outlet portion 64 of the filter 60 is sized so that its exterior surface is separated, at all points, from the interior surface of the intermediate portion and tapered lower end portion of the fluid inlet 30. The inlet portion 62 of the filter 60 is also appropriately sized so as to receive a connector of a suitable liquid conduit, such that the fluid inlet 30 communicates with a source of water during use.

As shown in FIGS. 1 and 2, the upper wall of the humidification chamber 10 includes a centrally positioned and downwardly extending guide sleeve 32 of cylindrical shape, which is of greater diameter than the fluid inlet 30 and extends co-axially therewith. Eight longitudinal ribs 33 are provided on the interior surface of the guide sleeve 32 at equiangularly spaced positions, so as to form channels for the water 20 being supplied through the fluid inlet 30 to flow down the exterior surface of the primary float 40 during use.

Figure 3:
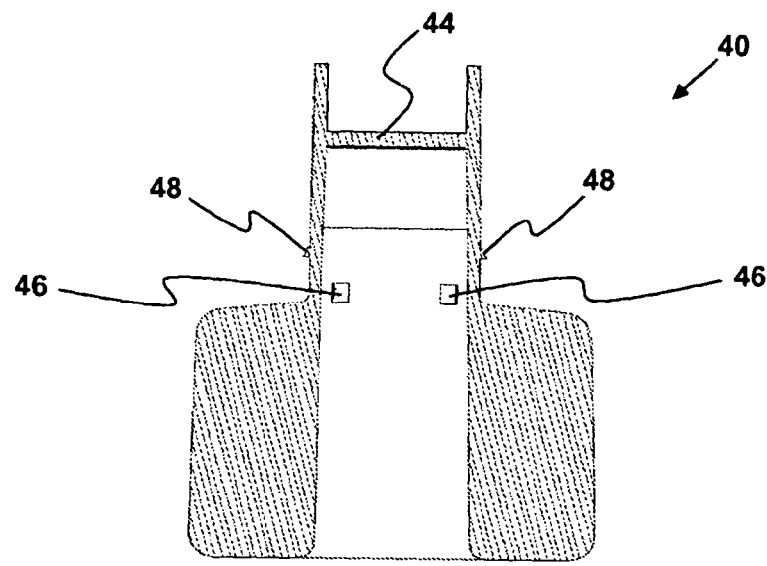
FIG. 3 is a cross-sectional view of the primary float.

A fluid inlet valve controls the flow of water 20 through the fluid inlet 30. The fluid inlet valve comprises a primary float 40, a valve cushion 42, and a secondary float 50. The primary float 40 is shown in isolation in FIG. 3, and comprises an upper portion and a lower portion, which are integrally formed in a plastics material using an injection moulding process that is described in published European patent application EP 1366881.

The upper portion of the primary float 40 is a generally cylindrical tube with relatively thin walls and a diameter that increases gradually and slightly from an open upper end to a open lower end. The exterior surface of the upper portion is highly polished to enable a low-friction slidable engagement with the guide sleeve 32, and includes a pair of circumferentially extending, and diametrically opposed, projections 48. These projections 48 are adapted to be engaged by the secondary float 50, as discussed in more detail below, and each comprises an operative lower surface that is orientated perpendicularly to the adjacent surface of the upper portion of the primary float 40.

A circular partition 44 extends across the interior of the upper portion of the primary float 40 so as to define a cylindrical recess in the upper surface of the primary float 40. In addition, the upper portion includes four openings 46, at equiangularly spaced positions, in a lower part of its wall below the circular partition 44.

The lower portion of the primary float 40 is also generally cylindrical in form, but has walls of greater thickness than those of the upper portion of the float 40. The plastics material of the lower portion has a foam-like structure with many pockets of gas trapped within the plastics material. The primary float 40 is located within the enclosure of the humidification chamber 10 such that the lower end of the primary float 40 rests on the base 14 of the humidification chamber 10 until a sufficient volume of water 20 is introduced into the humidification chamber 10, and the majority of the upper portion of the primary float 40 is received with a slidable fit within the guiding sleeve 46.

A valve cushion 42, which is formed of elastomeric material, has the form of a cup and is received with an interference fit within the cylindrical recess in the upper surface of the primary float 40. The open upper end of the valve cushion 42 has an outwardly extending flange that rests upon the rim of the upper portion of the primary float 40, and the base of the valve cushion 42 is separated from the circular partition 44 of the primary float 40 so as to allow deformation of the valve cushion 42 towards the central partition 44 during use.

Figure 4:
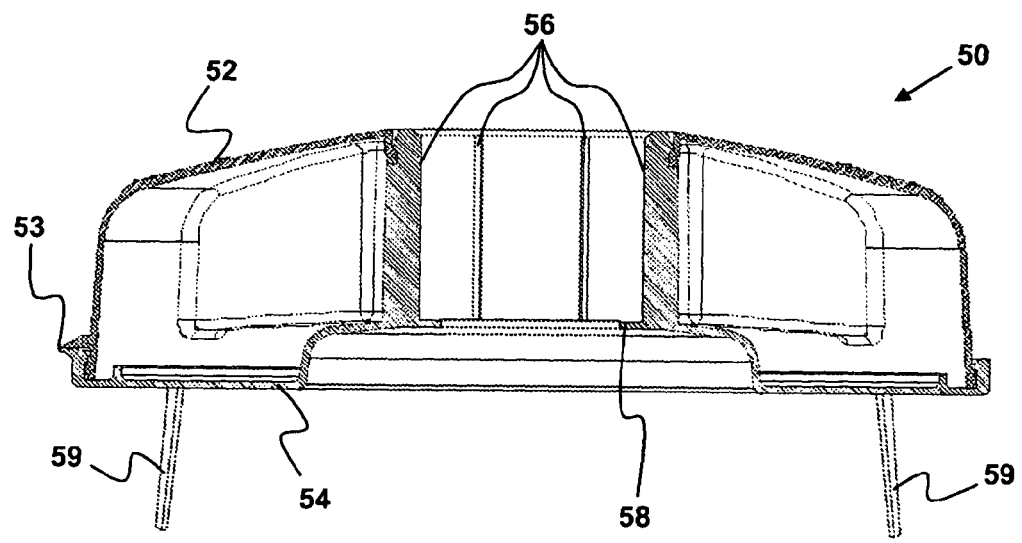
FIG. 4 is a cross-sectional view of the secondary float.

The secondary float 50 is shown in isolation in FIG. 4, and comprises upper and lower members 52,54 that are injection moulded as a single component, and joined by a hinge 53. The upper and lower members 52,54 together define an internal chamber that provides the secondary float 50 with approximately four times the buoyancy of the primary float 40. However, as shown in FIG. 2, a vent 55 is provided in the upper wall of the secondary float 50 to prevent the build-up of excessive pressure within the secondary float 50 during use.

The upper member 52 defines a side wall and an upper wall of the secondary float 50, and the lower member 54 defines an cylindrical inner wall and a base of the secondary float 50. The inner edge of the upper member 52, and the upper edge of the lower member 54, are formed with corresponding annular projections with enlarged heads that engage each other with a snap fit. Similarly, the outer edges of the upper and lower members 52,54 are formed with corresponding annular projections with enlarged heads that engage each other with a snap fit. In this way, the upper and lower members 52,54, joined by the hinge 53, are injection moulded as a single component, and the upper and lower members 52,54 are then rotated into engagement with each other, with a snap fit, so as to form the secondary float 50. The snap fit between corresponding projections is adapted to prevent the ingress of water into the internal chamber of the secondary float 50 during use. If necessary, however, the upper and lower members 52,54 are also glued together.

The upper member 52 of the secondary float 50 has a shape that conforms generally to the interior surface of the upper wall of the humidification chamber 10, such that the secondary float 50 is adapted to lie alongside the upper wall of the humidification chamber 10. In particular, the upper member 52 has a generally cylindrical, but slightly tapered, side wall and an annular upper wall, as shown most clearly in FIGS. 1 and 4. In addition, the upper member 52 comprises shallow depressions for accommodating the extensions 17 and baffles 18 of the inlet/outlet ports 16, as shown most clearly in FIG. 2, and more extensive recesses for accommodating the arcuate baffles 19 depending from the upper wall of the humidification chamber 10.

The lower member 54 comprises an annular base that is shaped so as to accommodate an upper part of the lower portion of the primary float 40, and a cylindrical inner portion that is adapted for slidable engagement with the exterior surface of the guide sleeve 32. The cylindrical inner portion has open upper and lower ends, and six longitudinal ribs 56 formed on its inner surface at equiangularly spaced positions. In addition, an annular flange 58 extends inwardly from the lower end of the inner portion of the secondary float 50, and includes an operative upper surface adapted to engage the projections 48 on the exterior surface of the primary float 40. The flange 58 also includes a series of openings 57 for enabling the throughflow of water 20 during use.

The lower member 54 also includes three legs 59 that rest upon the base 14 of the humidification chamber 10, and hence maintain the secondary float 50 at a minimum height, during normal operation. As shown in FIG. 2, the legs 59 each include an internal chamber that is in communication with the remainder of the interior of the secondary float 50.

Finally, the humidification chamber 10 includes a liquid level indicator 70 that enables a user to readily ascertain the level of the water 20. This liquid level indicator comprises an annular float 70 and suitable level indication marks (not visible in FIGS. 1 and 2), and is described in published European patent application EP 1347797.

The humidification chamber 10 is connected to a breathing circuit by attaching a gas inlet conduit (not shown in the Figures) to one of the inlet/outlet ports 16, and attaching a gas outlet conduit to the other inlet/outlet port 16. A heat source (not shown in the Figures) is placed in contact with the base 14 of the humidification chamber 10, so as to heat the water 20 within the humidification chamber 10 to a desired temperature.

A liquid conduit (not shown in the Figures) is then connected at one end to a source of water, and at the other end to the fluid inlet 30, so that water 20 is continuously supplied to the filter 60 and fluid inlet 30. When the source of water 20 is first connected to the humidification chamber 10, water 20 flows through the filter 60 and fluid inlet 30, fills the valve cushion 42, and then flows through the channels defined by the longitudinal ribs 33 of the guiding sleeve 32, through the openings 57 in the flange 58 of the secondary float 50, and down the exterior surface of the primary float 40 onto the base 14 of the humidification chamber 10. The humidification chamber 10 therefore begins to fill with water 20.

The source of water may be a flexible bag that is charged with water, or some other kind of water reservoir. Such sources often contain foreign objects, which may be present as a result of the manufacture, storage and/or previous use of the bag or reservoir. However, the filter 60 acts to prevent the passage of foreign objects through the fluid inlet 30 into the enclosure of the humidification chamber 10. In use, foreign objects collect, under the influence of gravity, in either the first collection chamber 68 in the inlet portion 62 of the filter 60, or the second collection chamber 69 in the outlet portion 64 of the filter 60. In each case, the collected foreign objects within the first and second collection chambers 68,69 are far removed from the open upper end of the outlet portion 64 and the apertures in the side wall of the outlet portion 64, and hence will not impede the flow of water through the filter 60 or interfere with normal operation of the valve mechanism.

When the water 20 within the humidification chamber 10 reaches a certain level, the primary float 40 is raised relative to the remainder of the humidification chamber 10 by its buoyancy. The primary float 40 is held in an upright position by the guiding sleeve 32. The primary float 40 will continue to rise until the water 20 reaches a sufficient level for the valve cushion 42 to be urged against the inner valve seat 34 of the fluid inlet 30 with enough force to form an effective seal, and hence prevent the inflow of water 20 through the lower opening of the fluid inlet 30. This configuration is shown in FIG. 1.

There will generally be some deformation of the valve cushion 42 towards the central partition 44 of the primary float 40 before an effective seal is formed between the valve cushion 42 and the inner valve seat 34, so that the inflow of water 20 into the humidification chamber 10 ceases. In the event that an effective seal is not formed between the valve cushion 42 and the inner valve seat 34, for instance due to the presence of foreign bodies on the operative surfaces of the valve cushion 42 and/or the inner valve seat 34, the primary float 40 will continue to rise and deformation of the valve cushion 42 will increase until the valve cushion 42 is urged against the outer valve seat 35 of the fluid inlet 30 with enough force to form an effective seal, and hence prevent the inflow of water 20 through the lower opening of the fluid inlet 30.

In use, gases intended for inhalation by a patient are supplied to the gas inlet conduit under positive pressure. The pressure differential created between the gas inlet conduit and the gas outlet conduit causes gases to flow from the gas inlet conduit, through the enclosure of the humidification chamber 10, to the gas outlet conduit. This causes water vapour within the chamber 10 to be entrained in the flow of gas through the humidification chamber 10, so that the gas within the gas outlet conduit has an increased humidity relative to the gas within the gas inlet conduit.

As water is entrained in the flow of gas through the humidification chamber 10, the level of the water 20 in the humidification chamber 10 will gradually reduce. The primary float 40 will therefore be lowered relative to the remainder of the humidification chamber 10. This will continue until the valve cushion 42 of the fluid inlet valve becomes separated from the lower opening of the fluid inlet 30, such that water 20 is allowed to flow into the humidification chamber 10 through the fluid inlet 30. As the level of water 20 increases once again, the primary float 40 will rise relative to the remainder of the humidification chamber 10. The primary float 40 will continue to rise until the water 20 reaches a sufficient level for the valve cushion 42 to be once again urged against the inner and/or outer valve seat 34,35 of the lower opening of the fluid inlet 30 with enough force to form an effective seal, and hence prevent the inflow of water 20 through the lower opening. In this way, the level of the water 20 is maintained relatively constant during use. In addition, the openings in the primary float 40 prevent the buoyancy of the primary float 40 being affected by air becoming trapped between the surface of the water 20 and the interior surface of the lower portion of the primary float 40.

In the event that the fluid inlet valve becomes damaged, for instance by small foreign objects limiting movement of the primary float 40 and/or damage to the primary float 40 reducing its buoyancy, the level of water 20 within the humidification chamber 10 will rise beyond the level at which the fluid inlet valve closes during normal operation. However, when the water 20 within the humidification chamber 10 reaches a certain level, the secondary float 50 is raised relative to the remainder of the humidification chamber 10 by its buoyancy, and held in an upright position by the guiding sleeve 32.

The secondary float 50 will continue to rise until the water 20 reaches a sufficient level for the flange 58 of the secondary float 50 to impinge upon, and hence engage, the projections 48 of the primary float 40. As the level of water 20 within the humidification chamber 10 increases, the upward buoyancy force imparted upon the secondary float 50, and hence the upward force imparted by the secondary float 50 upon the primary float 40, will increase until the primary float 40 is raised relative to the remainder of the humidification chamber 10. Since the secondary float 50 has a buoyancy that is approximately four times the buoyancy of the primary float 40, the upward force imparted by the secondary float 50 upon the primary float 40 will overcome common damage to the fluid inlet valve, such as limitation in the movement of the primary float 40 and/or damage to the primary float 40 reducing its buoyancy. The upward force imparted by the secondary float 50 upon the primary float 40 will cause the primary float 40 to be raised relative to the remainder of the humidification chamber 10 until the valve cushion 42 is urged against the inner valve seat 34 and/or the outer valve seat 35 of the fluid inlet 30 with enough force to form an effective seal, and hence prevent the inflow of water 20 through the lower opening of the fluid inlet 30, as discussed in detail above. This configuration is shown in FIG. 2.

The invention claimed is:

1. A humidification chamber for use in a breathing circuit to humidify gases before inhalation, the humidification chamber being adapted to contain a volume of liquid, and comprising a gas inlet port, a gas outlet port and a fluid inlet for introducing liquid into the humidification chamber, wherein the fluid inlet is provided with a filter member including a plurality of exit apertures for enabling flow of liquid through the filter member, and the filter member defines a collection chamber that is disposed below the exit apertures, in use, such that foreign objects in the liquid that are unable to pass through the exit apertures fall under the influence of gravity into the collection chamber.

2. A humidification chamber as claimed in claim 1, wherein the filter member is formed as a separate component from the fluid inlet.

3. A humidification chamber as claimed in claim 2, wherein the filter member is fixed relative to the fluid inlet so that the filter member defines a partition within the fluid inlet through which liquid flowing through the fluid inlet necessarily flows.

4. A humidification chamber as claimed in claim 1, wherein the filter member is formed of a relatively rigid plastics material, so that the filter member maintains its integrity and shape during normal use of the humidification chamber.

5. A humidification chamber as claimed in claim 1, wherein the exit apertures each have a length and/or width that is less than 1 mm.

6. A humidification chamber as claimed in claim 1, wherein the exit apertures each have a length and/or width that is less than 0.7 mm.

7. A humidification chamber as claimed in claim 1, wherein the exit apertures each have a length and/or width that is less than 0.5 mm.

8. A humidification chamber as claimed in claim 1, wherein the collection chamber is defined by a continuous wall of the filter member, and hence does not include any exit apertures.

9. A humidification chamber as claimed in claim 1, wherein the filter member comprises an inlet portion into which liquid from a source of liquid flows, and an outlet portion in which the exit apertures and the collection chamber are formed.

10. A humidification chamber as claimed in claim 9, wherein the outlet portion has the form of a liquid conduit having exit apertures within its side wall, and the collection chamber is defined by a closed end of the outlet portion.

11. A humidification chamber as claimed in claim 9, wherein the outlet portion is disposed generally vertically, and the collection chamber is formed at the lowermost end of the outlet portion.

12. A humidification chamber as claimed in claim 9, wherein the outlet portion is of tubular structure.

13. A humidification chamber as claimed in claim 9, wherein the outlet portion of the filter member extends along a central, longitudinal axis of the fluid inlet, and is separated from the interior surface of the fluid inlet at all points.

14. A humidification chamber as claimed in claim 9, wherein a wall of the filter member comprises a plurality of elongate openings, and a plurality of generally orthogonal ribs that are formed on a surface of that wall and extend across those openings, so as to define an array of exit apertures.

15. A humidification chamber as claimed in claim 14, wherein the outlet portion is of tubular structure, and the exit apertures are formed in a side wall of the outlet portion.

16. A humidification chamber as claimed in claim 14, wherein the orthogonal ribs are formed on the interior surface of the outlet portion.

17. A humidification chamber as claimed in claim 14, wherein the elongate openings extend along circumferences of the outlet portion, and the orthogonal ribs are orientated longitudinally along the outlet portion.

18. A humidification chamber as claimed in claim 9, wherein the inlet portion of the filter member is fixed to the fluid inlet, so that liquid supplied to the fluid inlet necessarily flows through the filter member.

19. A humidification chamber as claimed in claim 9, wherein the outlet portion of the filter member has reduced cross-sectional dimensions relative to the inlet portion, so that the outlet portion is separated from the interior surface of the fluid inlet.

20. A humidification chamber as claimed in claim 9, wherein the inlet and outlet portions of the filter member are both cylindrical, and have substantially co-extensive central axes.

21. A humidification chamber as claimed in claim 20, wherein the outlet portion extends a short distance into the interior of the inlet portion, so that a secondary collection chamber is defined about the entrance to the outlet portion.

22. A humidification chamber as claimed in claim 1, wherein the humidification chamber includes a valve for controlling the level of liquid within the humidification chamber.

23. A humidification chamber as claimed in claim 22, wherein the fluid inlet includes a primary valve seat, and the valve comprises an actuating member that is movable in response to a change in the level of liquid within the humidification chamber between an open configuration in which the actuating member is disengaged from the primary valve seat such that liquid is able to flow through the fluid inlet into the humidification chamber when the liquid within the humidification chamber is below a predetermined acceptable level, and a closed configuration in which the actuating member is engaged with the primary valve seat such that liquid is prevented from flowing through the fluid inlet into the humidification chamber when the liquid within the humidification chamber is at or above the predetermined acceptable level.

24. A humidification chamber as claimed in claim 23, wherein the fluid inlet includes a secondary valve seat, and the actuating member is deformable in response to an increase in the level of liquid within the humidification chamber above the predetermined acceptable level to a deformed configuration in which the actuating member engages the secondary valve seat such that liquid is prevented from flowing through the fluid inlet into the humidification chamber.

* * * * *